United States Patent
Smith et al.

(10) Patent No.: US 7,838,561 B2
(45) Date of Patent: Nov. 23, 2010

(54) METHOD FOR PREVENTING OR TREATING CARDIAC HYPERTROPHY

(75) Inventors: Susan M. Smith, Madison, WI (US); John W. Lough, Elm Grove, WI (US); George R. Flentke, Madison, WI (US)

(73) Assignees: Wisconsin Alumni Research Foundation, Madison, WI (US); MCW Research Foundation, Inc., Milwaukee, WI (US)

( * ) Notice: Subject to any disclaimer, the term of this patent is extended or adjusted under 35 U.S.C. 154(b) by 775 days.

(21) Appl. No.: 11/151,240

(22) Filed: Jun. 14, 2005

(65) Prior Publication Data

US 2005/0276804 A1    Dec. 15, 2005

Related U.S. Application Data

(60) Provisional application No. 60/578,877, filed on Jun. 14, 2004.

(51) Int. Cl.
*A61K 38/50* (2006.01)

(52) U.S. Cl. .......................... 514/613; 514/23; 514/252; 424/94.6

(58) Field of Classification Search ....................... None
See application file for complete search history.

(56) References Cited

PUBLICATIONS

Smith et al. Secretion of vitamin A and retinol-binding protein into plasma is depressed in rats by N-(4-hydroxyphenyl)retinamide (fenretinide). Jouranl of Nutrition, 1992, vol. 122(10): 1999-2009.*
Yamamoto et al. Interactions of Transthyretin (TTR) and Retinol-Binding Protein (RBP) in the Uptake of Retinol by Primary Rat Hepatocytes. Expertimental Cell Research 1997, vol. 234: 373-378.*
Green et al. Antisense oligonucleotides: an evolving technology for the modulation of gene, expression in human disease. J Am Coll Surg (2000), vol. 191: 93-105. Elsevier.*
Jen et al. Suppresion of Gene Expression by Targeted Disruption of Messenger RNA: Available Options and Current Strategies. Stem Cells (2000), vol. 18:307-319. AlphaMed Press.*
Caplen NJ. RNAi as a Gene Therapy Approach. Expert Opinon. Biol. Thera. (2003) vol. 3(4) 575-586. Ashley Publications Ltd.*
Novina et al. The RNAi Revolultion. Nature 2004, vol. 430: 161-164. Nature Publishing Group.*
Paroo et al. Challenges for RNAi in vivo. Trends in Biotechnology (2004), vol. 22(8) 390-394. Elsevier.*
Adams, A. RNA therapeutics enter clinical trials. Scientist (2005), vol. 19:Issue 1. Institute for Scientific Information.*
Wang et al. Effects of all-trans retinoic acid on angiostensin II induced myocyte hypertrophy. J. Appl. Physiol 2002, vol. 92, pp. 2162-2168.*
de Paiva et al. Ventricular remodeling induced by retinoic acid supplementation in adult rats. Am J Physiol Circ Physiol 2003, vol. 284, pp. H2242-H2246.*
Maier et al. Vitamin A for the heart: progress for cardiac hypertrophy regression? Am J Physiol Circ Physiol 2008, vol. 294, pp. H588-H589.*

Park et al. Identification of the genes involved in enhanced fenretinide-induced apoptosis by parthenolide in human hepatoma cells.*
Blomhoff, Fune. "Transport and metabolism of vitamin A", Nutrition Reviews, 1994; 52(2), S13.
Cobleigh, Melody A. "Brest Cancer and Fenretinide, an Analogue of Vitamin A", Leukemia,1994; 8(3), S59-S63, Macmillan Press Ltd, Chicago.
Colbert, Melissa C. "Retinoids and Cardiovascular Development Defects", Cardiovascular Toxicology.2002, 2(1), 25-39, Humana Press, Cincinnati.
Formelli et al., "Plasma Retinol Level Reduction by the Synthetic Retinoid Fenretinide: A One Year Follow- up Study of Breat Cancer Patients", Cancer Research. 1989; 49,6149-6152.
Formelli et al., "Five Year Administration of Fenretinide: Pharmacokinetics and Effects on Plasma Retinol Concentrations", Journal of Clinical Oncology, 1993; 11(10), 2036-2042.
Frey et al.,"Cardiac Hypertrophy: The Good, the Bad, and the Ugly", Annual Review Physiol 2003; 65, 45-79.
Kaiser-Kupfer et al.,"Abnormal Retinal Function Associated With Fenretinide, a Synthetic Retinoid", Arch Ophthalmol,1986; 104,69-70.
Kochhar,D M, "The Use of a Retinoid Receptor Antagonist in a New Model to Study Vitamin A-Dependent Developmental Events", The International Journal of Developmental Biology, 1998; 42(4),601-8.
Moon et al, Influence of 15 Retinoic Acid Amides on Urinary Bladder Carcinogenesis in the Mouse, Carcinogenesis 1982; 3(12), 1469-1472.
Moon et al.,"Inhibition of Carcinogenesis by Retinoids", Cancer Research(Suppl), 1983; 43,2469s-2475s.
Nagpal et al., "Recent Developments in Receptor-Selective Retinoids", Current Pharmaceutical Design, 2000;6,919-931.
Napoli,Joseph L, "Biochemical Pathways of Retinoid Transport, Metabolism, and Signal Transduction", Clinical Immunology and Immunopathology, 1996; 80(3), S52-S62.
Peng et al., "Pharmacokinetics of N-4-Hydroxyphenyl-Retinamide and the Effect of its Oral Administration on Plasma Retinol Concentrations in Cancer Patients", Int. J. Cancer, 1989; 43,22-26.
Ross,A.Catharine, "Vitamin A: Current Understanding of the Mechanisms of Action", Nutrition Today, 1991.
Sani et al., "N-(4 Hydroxyphenyl) Retinamide: Internactions with Retinoid-Binding Proteins/Receptors" Carcinogenesis, 1995; 16(10), 2531-2534.
Takahashi et al., "Effects on M5076-Hepatic Metastasis of Retinoic Acd and N-(4-Hydroxyphenyl) Retinamide, Fenretinide Entrapped in SG-Liposomes", Biol. Pharm. Bull., 2003;26(7), 1060-1063.

(Continued)

*Primary Examiner*—Kimberly Chong
(74) *Attorney, Agent, or Firm*—Kening Li; Pinsent Masons LLP

(57) ABSTRACT

A method for treating or preventing cardiac hypertrophy in a mammal, comprising manipulating levels of RBP, retinoids, or an affiliated signaling and regulatory pathway in the mammal. Preferably, the method comprises reducing or inhibiting the level of RBP or retinoids or their signaling pathway, or an affiliated signaling pathway, via a dietary, genetic, protein-based, or pharmacologic approach, or a combination thereof. Also disclosed are pharmaceutical composition suitable for the method.

4 Claims, No Drawings

OTHER PUBLICATIONS

Torrisi et al., "The Synthetic Retinoid Fenretinide Lowers Plasma Insulin-like Growth Factor I Levels in Breast Cancer Patients", Cancer Research 1993; 53, 4769-4771.

Altucci et al., "Leukemia: Beneficial actions of Retinoids and Rexinoids", The International Journal of Biochemistry & Cell Biology, 2004; 36, 178-182.

Apfel et al., "A Retinoic Acid Receptor α Antagonist Selectively Counteracts Retinoic Acid Effects", Proc. Natl. Acad. Sci. USA, 1992; 89, 7129-7133.

Conley et al., "Pilot Trial of the Safety, Tolerability, and Retinoid Levels of N-(4 hydroxyphenyl) Retinamid in Combination With Tamoxifen in Patients at High Risk for Developing Invasive Breast Cancer", Journal of Clinical Oncology, 2000; 18(2)(January), 275-283.

Dimitrov et al. "Alteration of Retinol-Binding-Protein Concentrations by the Synthetic Retinoid Fenretinide in Healthy Human Subjects", American Journal for Clinical Nutrition, 1990; 51,1082-7.

Giguere, Vincent., "Retinoic Acid Receptors and Cellular Retinoid Binding Proteins: Complex Interplay in Retinoid Signaling", Endocrine Reviews, 1994; 15(1), 61-79.

Holven et al., "Secretion of N-(4-Hydroxyphenyl) Retinamide-Retinal-Binding Protein From Liver Parenchymal Cells; Evidence for Reduced Affinity of the Complex for Transthyretin", Int. J. Cancer, 1997; 71, 654-659.

Klein et al. "Recruitment of Nuclear Receptor Corepressor and Coactivator to the Retinoic Acid Receptor by Retinoid Ligands", The Journal of Biological Chemistry, 2000; 275(25) (Jun. 23), 19401-19408.

Malpeli et al., "Retinoid Binding to Retinol-Binding Protein and the Interference with the Interaction with transthyretin", Biochimica et Biophysica Acta, 1996; 1294, 48-54.

Moon et al., "Dietary Retinoids and Carotenoids in Rodent Models of Mammary Tumorigensis", Breast Cancer Research and Treatment, 1997; 46,11181-189.

Oh et al., "Telomerase Reverse Transcriptase Promotes Cardiac Muscle Cell Proliferation, Hypertrophy, and Survival", PNAS, 2001; 98(18)(Aug. 28), 10308-10313.

Raffaghelto et al., "Immunoliposomal Fenretinide: A Novel Antitumoral Drug for Human Neuroblastoma",Cancer Letters, 2003; 197, 151-155.

Zhou et al., "Retinoid-Dependent Pathways Suppress Myocardial Cell Hypertrophy", Proc. Natl. Acad. Sci. USA, 1995; 92, 7391-7395.

* cited by examiner

METHOD FOR PREVENTING OR TREATING CARDIAC HYPERTROPHY

CROSS REFERENCE TO RELATED APPLICATIONS

This application claims the priority of U.S. Provisional Application No. 60/578,877, filed Jun. 14, 2004, the disclosure of which is expressly incorporated by reference herein.

FEDERAL GOVERNMENT INTEREST

This invention was made with United States government support under a grant from the National Institutes of Health (NIH), Grant Number NIH HL61911. The United States has certain rights to this invention.

BACKGROUND OF THE INVENTION

Cardiac hypertrophy is the heart's response to a variety of extrinsic and intrinsic stimuli that impose increased biomechanical stress. The increased workload on the heart and a progressive decrease in its pumping ability, cause an increase in cardiomyocyte size, enhanced protein synthesis, and a higher organization of the sarcomere. Initially, the increased workload that results from high blood pressure or loss of contractile tissue induces compensatory cardiomyocyte hypertrophy and thickening of the left ventricular wall, thereby enhancing contractility and maintaining cardiac function. However, over time, the left ventricular chamber dilates, systolic pump function deteriorates, cardiomyocytes undergo apoptotic cell death, and myocardial function progressively deteriorates.

While physiological cardiac hypertrophy may represent a positive adaptive response to increased workload, pathological hypertrophy is a principal risk factor for the development of congestive heart failure and subsequent cardiac death. In fact, congestive heart failure is a leading cause of death in industrialized nations.

It is recognized that in most instances hypertrophy is not a compensatory response to the change in mechanical load, but rather is a maladaptive process. Accordingly, modulation of myocardial growth without adversely affecting contractile function is increasingly recognized as a potentially auspicious approach in the prevention and treatment of heart failure.

Factors that underlie congestive heart failure include high blood pressure, ischemic heart disease, exposure to cardiotoxic compounds such as anthracycline antibiotics, and genetic defects known to increase the risk of heart failure.

The stimuli inducing cardiac hypertrophy include various growth factors, hormones, and cytokines such as endothelin-1, angiotensin II, insulin-like growth factor-1, myotrophin, and cardiotrophin-1. Mechanical stress is another important stimulus for cardiac hypertrophy. Mechanical stress is considered to be the trigger inducing a growth response in the overloaded myocardium. Furthermore, mechanical stress induces the release of growth-promoting factors, such as angiotensin II, endothelin-1, and transforming growth factor-β, which provide a second line of growth induction.

By using an in vitro neonatal cardiomyocyte culture system, it has been demonstrated that mechanical stretch induces signal transduction characterized by simultaneous activation of multiple second messenger pathways, such as phospholipases (C, D, and A2), protein kinase C (PKC), the JAK/STAT pathway, mitogen-activated protein (MAP) kinase cascades, and calcium/calmodulin-dependent protein phosphatase calcineurin pathway. Molecules in these pathways may be targets for therapies designed to prevent the progression of cardiac hypertrophy.

Signaling pathways related to cardiac hypertrophy have been reviewed in Frey and Olson, 2003, Cardiac hypertrophy: the good, the bad, and the ugly. Annu. Rev. Physiol. 65:45-79, which is incorporated herein by reference in its entirety.

Vitamin A (retinol) and its natural and synthetic derivatives (retinoids) participate in a wide range of biological processes, including vision, neoplasia, embryonic development, normal reproductive function, regulation of epithelial and hematopoietic cellular differentiation, and cardiovascular development. Retinoic acid (RA), the active metabolite of vitamin A, is the main signaling retinoid in the body. RA functions by binding to nuclear receptor proteins.

SUMMARY OF THE INVENTION

The present invention provides for a method for treating or preventing cardiac hypertrophy in a mammal, especially in a human, or a higher vertebrate such as birds. The method of the present invention may be used for the treatment of pathological hypertrophy, chronic heart failure, restrictive cardiomyopathies, valvuloseptal disorders, ischemic heart disease, emphysema, atherosclerosis, amyloidosis, viral myocarditis, cardiac dilatation, and genetic syndromes of dysfunctional heart action.

The method comprises reducing levels of retinol binding protein (RBP) or levels of retinoid in the mammal, or inhibiting the function of RBP or retinoid in the mammal, or inhibiting the function or activity of the retinoic acid (RA) signaling pathway or pathways that are regulated by retinoid signaling or related regulatory pathway.

In one embodiment, a retinol structural antagonist, or a retinoid receptor antagonist, is administered to the mammal to block delivery of retinol by RBP, to the heart of the mammal, thereby reducing the progression or severity of pathological cardiac hypertrophy in the mammal. For example, the binding of RBP with transthyretin (TTR) is inhibited, or the expression of RBP or TTR or both is inhibited, such as via a suitable antisense nucleic acid molecule, or a suitable siRNA molecule. Alternatively, the function of RBP or TTR or both is inhibited via a suitable antibody, or a small molecule antagonist.

According to a preferred embodiment, an effective amount of an retinoid antagonist, such as N-[4-hydroxyphenyl]retinamide, is administered to the mammal.

In another embodiment, the expression or function of a retinoid receptor is inhibited for example, by a suitable antisense nucleic acid molecule, or a suitable siRNA molecule, a suitable antibody, or a small molecule antagonist. In a specific embodiment, the retinoid receptor is an RAR (e.g. RAR-α, RAR-β, or RAR-γ) or an RXR (e.g. RXR-α, RXR-β or RXR-γ). For example, the formation of an RXR/RXR, an RXR/RAR or an RAR/RAR dimer is inhibited.

The present invention also provides pharmaceutical compositions for the treatment of pathological hypertrophy, chronic heart failure, restrictive cardiomyopathies, valvuloseptal disorders, ischemic heart disease, emphysema, atherosclerosis, amyloidosis, viral myocarditis, cardiac dilatation, or genetic syndromes of dysfunctional heart action, the pharmaceutical composition comprising an effective amount of a retinoid or a RAR receptor antagonist, and a pharmaceutically acceptable excipient.

DETAILED DESCRIPTION OF THE INVENTION

Prior to the instant invention, it was generally accepted that retinoids had an anti-hypertrophy effect. See e.g. Wendler et al., 2003, Increased fibronectin deposition in embryonic hearts of retinol-binding protein null mice, Circulation Res. 92:920-928, which is also incorporated herein by reference. Evidence in the scientific literature links deficiency of vitamin A or embryonic deletion of selected retinoid receptors to a variety of defects in cardiovascular development. In the post-development period, retinoids are believed to be required for the proper functioning of a number of organs (skin, lung, liver, neuronal and immune systems) and have important regulatory activity in the cardiovascular system. In addition, retinoids have been shown to have significant anti-hypertrophic effects in neonatal cardiomyocytes. It was also observed that RA appears to have suppression effects on cyclic stretch-induced cardiac hypertrophy.

The signaling mechanisms of the purported RA-induced inhibitory effects on the hypertrophic process, however, have never been clear. Although numerous studies have focused on characterization of the intracellular signal transduction molecules that promote cardiac hypertrophy, little work has focused on signaling pathways that might negatively regulate hypertrophy.

The present inventors surprisingly discovered that inhibition of retinoic acid (RA) signaling pathway or related signaling pathways reduce cardiac hypertrophy, and is beneficial to cardiomyopathy patients. For example, the levels of retinol binding protein (RBP) can be reduced or its function inhibited.

The levels of RBP, retinoids, and their affiliated signaling and regulatory pathways can be manipulated by dietary, genetic, protein-based, and pharmacologic approaches to impact the induction or repression of stress-response pathways in heart, or in tissues that influence stress-responses of heart, such as the vascular, pulmonary, renal, hepatic, or nervous system.

In one embodiment, a retinol structural antagonist is used to block RBP's delivery of retinol to heart, and thus reduce the progression and/or severity of pathological cardiac hypertrophy.

In another embodiment, a retinoid receptor antagonist is used to enhance the expression of mediators for physiological hypertrophy responses, which would then support or improve myocardiocyte function in dilated cardiac failure.

In a further embodiment, a peptide or small molecule that disrupts RBP interactions with transthyretin (TTR), is administered to a patient in need thereof, thus blocking RBP-TTR interaction and allowing free RBP to be lost more rapidly in kidney filtrate, shortening its half-life in the serum and reducing the delivery of retinol to the heart. This is used to slow or reverse the cardiomyofibril enlargement that occurs in hypertension diseases.

In yet another embodiment, a retinoid antagonist is used that would enhance Serca-2a expression in the heart, and facilitate calcium handling and sequestration within the cardiomyocyte or smooth muscle, thus improving muscle relaxation and contractile efficacy in conditions of dysfunctional calcium handling.

The present invention provides treatment or ameliorative methods beneficial for numerous situations in which an improvement in cardiac function would be warranted, including but not limited to pathological hypertrophy, chronic heart failure, restrictive cardiomyopathies, valvuloseptal disorders, ischemic heart disease, emphysema, atherosclerosis, amyloidosis, viral myocarditis, cardiac dilatation, and genetic syndromes of dysfunctional heart action. The method of the present invention also can be applied to situations where the heart is not the primary affected organ, but in which the ability to improve heart function would be beneficial to the patient. These include renal failure, fibrosis of liver or lungs, and dysfunction of smooth muscle action. This discovery has numerous applications for affecting normal cardiovascular function, and for treating adverse syndromes and conditions in which the impairment of cardiac function is a direct or indirect consequence of that syndrome or condition.

The present invention provides methods for directly targeting hypertrophic cardiomyopathy, including but not limited to: (1) hypertensive cardiomyopathy, which is one of the most significant cardiomyopathies, and associated damage from essential hypertension and arteriosclerosis; (2) genetic forms of hypertrophic cardiomyopathy. Many genetic loci are known to be associated with genetic cardiac disorders, including at least eight specific genes with a total of 125 mutations as of 2001: beta-myosin heavy chain, troponin T; troponin I; alpha-tropomyosin; myosin binding protein C; essential myosin light chain; and regulated myosin light chain actin; and syndromes with unknown genetic locus (e.g. Wolff-Parkinson-White Syndrome); (3) structural cardiomyopathies, such as aortic stenosis (including mitral valve abnormalities), and (4) hypertrophic cardiomyopathy associated with certain disease states, such as hyperparathyroidism, neurofibromatosis, generalized lipodystrophy, lentiginosis, pheochromocytoma, Friedrich's ataxia, Noonan syndrome, amyloid diseases, glycogen storage disease III. The method of the present invention may also be used to prevent sudden death in competitive sports caused by cardiomyopathy.

In another preferred embodiment, the method of the present invention may be used to achieve improved cardiovascular function which would be advantageous. The method may be used to treat or prevent dilated cardiomyopathy, including those caused by genetic defects (e.g. dystrophin gene); viral, bacterial, or parasitic myocarditis; ischemic cardiomyopathy; autoimmune disorders (e.g. Lupus); by alcohol and other drug abuse; by toxicants such as cobalt, lithium, lead, drugs (e.g. anthrocyclines, antiretrovirals).

The method may be used to treat or prevent restrictive cardiomypathy, including those of genetic origin (e.g. amyloidosis caused by a defect of the transthyretin gene), or caused by a disease, such as diabetes, Gaucher disease, Hurler Disease, hemochromatosis, Fabry Disease, glycogen storage disease III, sarcoidosis, endomyocardial fibrosis, or cancer. The method may be used to treat or prevent restrictive cardiomypathy caused by cancer, or by toxicants such as anthrocyclines or choroquine, or by radiation.

Target Proteins or Genes

The present invention contemplates that every element of the signaling pathway can be blocked or otherwise targeted to achieve the desired effect of inhibiting or preventing cardiac hypertrophy.

One target is the retinol binding protein (RBP), which is a small molecular weight protein (21 kDa) that binds retinol and functions to transport retinol to the cell. RBP may act to transport other molecules whose identities are not currently known.

In another embodiment, the method of present invention targets a larger protein molecule, transthyretin (TTR, formerly called prealbumin). TTR forms a complex with RBP, and prevents the loss of RBP through the renal glomeruli and stabilizes the binding of retinol to RBP.

Yet a further target is one of the retinoid receptors. Retinoic acid (RA) and its synthetic analogs (retinoids) function through activating two distinct classes of nuclear receptor proteins, the retinoic acid receptors (RARs) (Giguere et al. (1990) Mol. Cell. Biol. 10:2335-2340), whose encoded proteins bind both all-trans RA (atRA) and 9-cis RA; and the retinoid X receptors (RXRs) (Mangelsdorf et al. (1992) Genes Dev. 6:329-344) that preferentially bind 9-cis RA. These retinoid receptors belong to the steroid/thyroid hormone receptor super family (Evans (1988) Science 240:889-895), and each class has three receptor subtypes, RAR-α, RAR-β, and RAR-γ and RXR-α, RXR-β and RXR-γ. A functional receptor capable of activating DNA transcription is either a homodimer (RXR/RXR) or a heterodimer (RAR/RXR). These ligand-activated retinoid receptors act as transcription factors which bind to RA response elements in the promoters/enhancers of numerous target genes, leading to transcriptional stimulation or repression.

One function of RXR is to act as an auxiliary receptor for several nuclear receptors, including the RARs, thyroid hormone receptors and vitamin D receptor. Heterodimers of RXR with these receptors form in solution (Zhang et al. (1992a) Nature 355:441-446) and bind selectively with high affinity to specific hormone response elements (Hermann et al. (1992) Mol. Endocrinol. 6:1153-1162). RXRs also function independently as homodimers (Zhang et al. (1992b) Nature 358:587-591) which form in the presence of the 9-cis isomer of all-trans RA, and have different response element specificities than the RAR:RXR heterodimers (Hermann et al. (1992) supra; Zhang et al. (1992b) supra). In contrast, RARs bind both ligands with high affinity (Heyman et al. (1992) Cell 68:397-406).

Recently, a truncation deletion mutant of the RAR-α receptor has been described which functions as a transdominant negative mutant, hRXRα403, able to block normal retinoic acid induced transcriptional transactivation through both the RXR/RAR heterodimer and the RXR homodimer pathways (Damm et al. (1993) Proc. Natl. Acad. Sci. U.S.A. 90:2989-2993).

RARs and RXRs are activated upon binding to an RA ligand. Enzymes that synthesize RA ligand from retinol include retinol dehydrogenase, retinaldehyde dehydrogenase, retinol reductases, and cytochrome P450s. Enzymes that catabolize and remove RA include cytochrome P450 26A and 26B. It is known that these enzyme activities can be manipulated to control cellular RA levels (e.g. via knockout, RNAi, small molecule drugs).

Transcriptional activity of retinoid receptors and related receptors are governed by histone acetylases (HAac) and histone deacetylases (HDAc). HAc catalyzes the acetylation of histone proteins; this blocks heterochromatin assembly and opens the promoter region, revealing the retinoid response element (RARE) and permitting transcription. HDAc deacetylates the histone, allowing chromatin winding and silencing retinoid-receptor-mediated transcription. These enzymes can be manipulated to control retinoid signaling.

Cytosolic proteins control the intracellular levels of retinol and RA, affecting the ability of RA to be synthesized and then travel to the nucleus to mediate transcription by RAR and RXR. These proteins include cellular retinol binding proteins (types CRBP I, CRBP II, CRBP III) and cellular retinoic acid binding proteins (CRABP I, CRABP II). It is known that the levels and activities of these proteins can be manipulated to control retinoid and retinoid receptor signaling.

Some tissues, notably the eye, contain a cell-surface receptor for RBP, and this receptor can facilitate the cellular uptake of retinol from RBP. Manipulating the availability or activity of this receptor will allow the manipulation of retinoid signaling.

Signaling pathways whose receptors and their binding proteins that compete for transcriptional or other regulatory complexes that are shared with the RA receptors or signals may also be modulated to achieve similar effects of inhibiting cardiac hypertrophy. For example, hormones, such as vitamin D, thyroid hormone, 9-cis-retinoic acid, and the many ligands for the nuclear peroxisome proliferator-activated receptors (PPARs) alpha, beta, and gamma, directly compete with and overwhelm the retinoid/RAR signaling pathways. Another known RAR antagonist is COUP-TF, which has no known ligand. It is known that too little retinoid/RBP could allow other hormones (specifically thyroid hormone, vitamin D, 9-cis-retinoic acid, and PPAR ligands) to dominate when otherwise they would not if retinoid/RBP was normal. These pathways can be activated to override retinoid signaling, for instance, by adding an agonist of those receptors (e.g. thyroid hormone, vitamin D, PPAR ligands) to preferentially activate those pathways and reduce retinoid signaling. Alternatively, constitutively active versions of these other receptors are known to exist and can be used.

An alternate approach is to block the intestinal absorption of retinoids into the body, or to block the packaging and transport of dietary retinoids into the lymph or bloodstream. For example, by altering the activity of the retinoid esterases or carotenoid cleavage enzymes that convert dietary retinoids into forms that can be packaged and transported by lipoproteins or albumin. Alternatively, an antibody or its fragment can be administered to selectively bind and sequester a retinoid, such as retinoic acid, or a small molecule transported by RBP.

Retinoids may also be sequestered in storage sites such as liver or adipose, thus prevented from being released to the body. For example, altering the activity of the retinoid esterases that convert retinol to its retinyl ester storage form in liver stellate cells or adipocytes.

Table 1 below lists some of the possible target human genetic loci and their sequence and annotation information, as embodied in their Genbank database accession numbers. All information associated with the accession numbers, including their DNA or RNA sequences, is incorporated herein expressly by reference.

Methods For Inhibiting the Target Protein or Gene Functions

Retinoid Receptor Antagonists

In one embodiment, the present invention uses a retinoid receptor antagonist to inhibit the target protein or gene function. Retinoid receptor antagonists are a class of compounds that bind to retinoic acid receptors (RARs) or 9-cis-retinoic acid receptors (RXRs), but do not activate the receptor's gene transcriptional activity. Table 2 lists some of the known RAR antagonists.

Several classes of retinoid antagonists are known to those skilled in the art. "Classic" retinoic acid receptor antagonists compete with the natural ligand, all-trans-retinoic acid, for the receptor's binding site, and thus prevent transcriptional activation. Inverse agonists silence or significantly reduce RAR- or RXR-mediated gene transcription by recruiting co-repressors to the receptor's gene transcriptional complex. A third class, the retinoid-related molecules (RRM), weakly bind the RARs and RXRs, yet are potent biological effectors, notably as pro-apoptosis agents. RRMs include 4-hydroxyphenylretinamide, AGN 193198, and CD437. Their mechanism of action is unclear.

TABLE 1

Target Genes and Their Database Accession Numbers

| Protein Names or Functions | Accession Number |
|---|---|
| Retinol Binding Protein | |
| Homo sapiens retinol binding protein 7, cellular (RBP7) | NM_052960 |
| Homo sapiens retinol binding protein 1, cellular (RBP1) | NM_002899 |
| Homo sapiens retinol binding protein 3, interstitial (RBP3) | NM_002900 |
| Homo sapiens retinol binding protein 2, cellular (RBP2) | NM_004164 |
| Homo sapiens retinol binding protein 4, plasma (RBP4) | NM_006744 |
| Homo sapiens retinol binding protein 5, cellular (RBP5) | NM_031491 |
| Homo sapiens retinaldehyde binding protein 1, mRNA | BC004199 |
| Homo sapiens retinaldehyde binding protein 1 (RLBP1) | NM_000326 |
| Homo sapiens cellular retinoic acid binding protein 1 (CRABP1) | NM_004378 |
| Homo sapiens cellular retinoic acid binding protein 2 (CRABP2) | NM_001878 |
| Retinoid Receptor | |
| Homo sapiens RAR-related orphan receptor A (RORA) | NM_134260 |
| Homo sapiens RAR-related orphan receptor A (RORA) | NM_134261 |
| Homo sapiens RAR-related orphan receptor A | NM_134262 |
| Homo sapiens retinoic acid receptor, alpha (RARA) | NM_000964 |
| Homo sapiens retinoic acid receptor, beta (RARB) | NM_000965 |
| Homo sapiens retinoic acid receptor, gamma (RARG) | NM_000966 |
| Homo sapiens RAR-related orphan receptor A (RORA) | NM_002943 |
| Homo sapiens retinoic acid receptor, beta (RARB) | NM_016152 |
| RXR-α receptor | NM_002957 |
| RXR-β receptor | NM_021976 |
| RXR-γ receptor | NM_006917 |
| Retinaldehyde Dehydrogenase | |
| RALDH-1 | NM_003888 |
| RALDH-2 | NM_170696 |
| RALDH-3 | NM_170697 |
| Cytochrome P450 (retinoid degrading systems) | |
| CYP26A1 | NM_000783 |
| CYP26C1 | NM_183374 |
| CYP26S1 | NM_030622 |
| Examples of retinoid dehydrogenases | |
| RDH5 | NM_002905 |
| RDH8 | NM_015725 |
| RDH10 | NM_172037 |
| RDH11 | NM_016026 |
| RDH12 | NM_152443 |
| RDH13 | NM_138412 |
| RDH14 | NM_020905 |
| Alcohol Dehydrogenase with retinol as a substrate | |
| ADH4 | NM_000670 |
| ADH7 | NM_000673 |
| NADP-dependent retinol dehydrogenase (DHRS7) | NM_005771 |
| NADP-dependent retinol dehydrogenase (DHRS4) | NM_021004 |
| Microsomal AND-dependent retinol dehydrogenase (RODH4) | NM_003708 |
| Lecithin retinol acyltransferase (LRAT) | NM_004744 |

In addition to compounds that directly bind and antagonize RAR action, RAR can also be antagonized by RXR-specific retinoids. These latter have the potential to antagonize RAR activity through binding competition that favors creation of RXR-RXR homodimers over RAR-RXR heterodimers (Hembree et al., 1996, Retinoid X receptor-specific retinoids inhibit the ability of retinoic acid receptor-specific retinoids to increase the level of insulin-like growth factor binding protein-3 in human ectocervical epithelial cells. Cancer Res. 56:1794-1799).

Retinoid receptor antagonists were developed, in part, to address problems of toxicity in clinical uses of RA, notably skin pathologies. The intent was to co-deliver the RA agonist with antagonist "X" that would counter some of RA's side toxicities. None of these antagonists are known to have been tested clinically for this purpose.

Noteworthy retinoid antagonists include AGN 193109, a pan-RAR antagonist that is perhaps the best characterized with respect to its in vivo and in vitro actions. It competes for retinoid receptor binding, with half-maximal activity in a 1:1 molar ratio with ligand, and full repression at a 10:1 molar ratio. A second pan-RAR antagonist, AGN 194310, entered preclinical trials to obviate retinoid agonist toxicity (Johnson et al. 1999b, Synthesis and biological activity of high affinity retinoic acid receptor antagonists. Bioorg Med Chem 7:1321-1338). A third compound "3a" is an especially promising pan-RAR antagonist with respect to potency (Vuligonda et al., 1999, A new class of potent RAR antagonists: dihydroanthracenyl, benzochromenyl and benzothiochromenyl retinoids. Bioorg Med Chem Lett 9:743-748.)

An alternate approach is to utilize retinoid compounds that have narrow specificity for retinoid receptor binding. Such compounds would allow normal retinoid functions to continue for those processes using RARs or RXRs that are not targeted by the antagonist. There are noteworthy lead compounds in this category. As one example, AGN 194301 selectively silences RARα-dependent activities at a 0.1:1 molar ratio. Johnson et al. (1999a) (High affinity retinoic acid receptor antagonists: analogs of AGN 193109. Bioorg Med Chem Lett 9:573-576.) presents retinoid antagonists derived from AGN 193109, but none have the parent compound's potency. AGN 194431 is selective for RARβ and RARγ.

TABLE 2

Known Retinoid Receptor Antagonists

| Compound | Receptor Specificity | RARα Kd, nM | RARβ Kd, nM | RARγ Kd, nM |
|---|---|---|---|---|
| All-trans-retinoic acid | RARαβγ (endogenous ligand) | 15 | 13 | 18 |
| Allergan, Inc. | | | | |
| AGN 193109[1] | RARαβγ | 16 | 7 | 7 |
| AGN 194310[2] | RARαβγ | 3 | 2 | 5 |
| AGN 193491[3] | RARαβγ | 15 | 13 | 18 |
| AGN 194301[2,3] | RARα | 3 | 320 | 7250 |
| AGN 194574[3] | RARα | 2 | 900 | 10600 |
| AGN 193618[3] | RARα | 6 | 620 | 860 |
| AGN 194202[3] | RARα | 32 | 2250 | >30,000 |
| AGN 194431[2] | RARβγ | 300 | 6 | 70 |
| AGN 193840[1] | RARαβγ | 85 | 52 | 82 |
| Bristol-Myers Squibb | | | | |
| BMS 189453[4,5] | RARαγ | ~15 antagonist | ~13 agonist | ~20 antagonist |
| BMS 185411[4,5] | RARα | ~150 antagonist | ~1300 agonist | ~20,000 weak agonist |
| BMS 614[4] | RARα | antagonist (2.5) | not bound | not bound |
| BMS 681[4] | RARβ | agonist | agonist | antagonist |
| Roche | | | | |
| Ro 41-5253[6] | RARα | 60 | 2400 | 3300 |
| Ro 46-5471[6] | RARα | 27 | 5100 | 240 |

References for Table 2:
[1]Klein et al., 1996, J. Biol. Chem. 271: 22692-22696.
[2]Hammond et al., 2002, Anti-Cancer Drugs 13: 781-790.
[3]Teng et al., 1997, J. Med. Chem. 40: 2445-2451.
[4]Chen et al., 1996, Nature 382: 819-822.
[5]Chen et al., 1995, EMBO J 14: 1187-1197.
[6]Keidel et al, 1994. Mol Cell Biol 14: 274-298.

BMS 189453 has a complex profile, with both antagonist and agonist action. Specifically, it is an RARα and RARγ antagonist, and a weak RARβ agonist; it suppresses RAR-dependent transcription at a ratio of 1000:1 (Yang et al. 1999, Retinoic acid receptor antagonist BMS453 inhibits the growth of normal and malignant breast cells without activating RAR-dependent gene expression. Breast Cancer Res Treat 56:277-291.) In vitro, it does not transactivate the RARs. However, like other RA agonists, it also represses AP-1 activity and therefore acts as a retinoid in this non-transcriptional role (Yang et al. 1999, supra). Thus, this compound dissociates the trans-activation from the AP1-repressive actions of retinoids. Its mixed agonist/antagonist properties should be considered when evaluating the in vivo studies of this compound.

Many RAR receptors have undergone various stages of in vivo animal tests for their potential as targets for treatment. Some of these tests are reviewed below.

Cardiogenesis—BMS 189453 was used as an RAR antagonist to suppress myocardiogenesis in the gastrulation-stage zebrafish embryo. This demonstrated that myocardiogenesis requires RA signaling via its receptors (Keegan et al. 2005, Retinoic acid signaling restricts the cardiac progenitor pool. Science 307:247-249).

Epidermis—Topical application of AGN 193109 (0, 1.44, 7.2, 36.0 μmol/kg/day) in mice counteracts the toxicity symptoms of retinoic acid (TTNPB) toxicity, with respect to cutaneous irritation, weight loss, and mortality (Standeven et al. 1996, Specific antagonist of retinoid toxicity in mice. Tox Appl Pharm 138:169-175). This paper indicates that topical antagonist can counteract activities of systemic retinoid.

Epidermis—A novel lead compound, "3a" from Allergan is described in Vuligonda et al. (1999, supra). It has potent antagonist actions against all three RARs (pan-RAR antagonist; Kd 5-6 nM) and is favorably comparable to AGN 193109. It has low toxicity in topical application of mice (3.6 nmol/25 g; 1:2 against TTNPB).

Granulopoiesis—Mice were treated orally with AGN 194310 (0.5 mg/kg/day for 10 days) for 10 days (Walkley et al. 2002, Retinoic acid receptor antagonism in vivo expands the numbers of precursor cells during granulopoiesis. Leukemia 16:1763-1772). This dose was sufficient to elevate the frequency of bone marrow granulocytic precursors, showing a requirement for RAR signaling in granulocyte differentiation. Importantly, mice did not show signs of ill health or abnormal pathology in this treatment.

Pregnancy—In the pregnant mouse, 1 mg/kg AGN 193109 as a single oral dose was sufficient to antagonize retinoid-specific events in craniofacial development (Kochhar et al. 1998, The use of a retinoid receptor antagonist in a new model to study vitamin A-dependent developmental events. Int. J. Dev. Biol. 42:601-608). Later in development, a single oral dose of 100 mg/kg suppresses the hormone action of RA in skin. AGN 193109 readily crosses the placenta and can accumulate in the conceptus to affect RAR-mediated gene transcription.

Arthritis—in mouse and rat, BMS 189453 (ip, 15 mg/kg/d) delayed the onset, severity, and progression of inflammation and joint erosion in two independent models of autoimmune (rheumatoid) arthritis (Beehler et al., 2003, Inhibition of disease progression by a novel retinoid antagonist in animal models of arthritis. J. Rheumatol. 30:355-363). Overt toxicity or hypovitaminosis A was not observed in either study. Also, BMS 189453 (0.01 to 10 μM) suppresses gene expression of pro-inflammatory collagenase in cultured rabbit HIG-82 synovial fibroblasts (Beehler et al. 2003, supra). At 1 μM it also inhibits mammary epithelial cell growth, through effects not on RAR-mediated transcription, but through a distinct mechanism that involves TGFβ induction (Yang et al., 2001, The retinoic acid receptor antagonist, BMS453, inhibits normal breast cell growth by inducing active TGFβ and causing cell cycle arrest. Oncogene 20:8025-8035).

Renal Disease—Rats administered BMS 189453 (20 mg/kg/day, 7 days, subcutaneous) did not show toxicity with respect to altered eating or drinking, posturing or behavior, or weight loss (Lehrke et al., 2002, Retinoid receptor-specific agonists alleviate experimental glomerulonephritis. Am. J. Physiol. Renal Physiol. 282:F741-F751). In this study it acted as an agonist to reduce the progression of experimental glomerulonephritis. (Recall it has joint antagonist/agonist action.)

Testicular Toxicity—It should be noted that BMS 189453 caused the atrophy and degeneration of testicular cells in rats (2, 10, 50 mg/kg for 1, 3, 7 days) and in rabbits (2, 10, 50 mg/kg orally for 1 wk) (Schulze et al., 2001, BMS-189453, a novel retinoid receptor antagonist, is a potent testicular toxin. Toxicol. Sci. 59:297-308). This effect was highly selective, because these doses were not overtly toxic. Overt toxicity was observed in rats given 240 mg/kg daily for 30 days. However, 30 days after ceasing treatment, testicular atrophy was seen at even low doses (2-50 mg/kg). The testis is a known target of retinol (pro-hormone RA) and RA. It was not ascertained whether the toxicity was due to the compound's RAR antagonist properties, or to its repression of AP-1 action. Testicular degeneration does occur at high RA intakes. The authors speculate the effects were due to BMS453 causing long-term retinoid deficiency in the testes, with depletion of its germ cells.

Chondrogenesis—Repression of RAR signaling is required for chondrogenesis to proceed. Both AGN 194310 (50 nM) and AGN 194301 (1 μM) overcome RA signaling and permit the differentiation of mouse limb bud chondrocytes, with commensurate induction of Sox9 (Weston et al., 2002, Requirement for RAR-mediated gene repression in skeletal progenitor differentiation. J. Cell Biol. 158:39-51). These effects were mimicked by transfection with a dominant negative RAR.

Bladder Carcinoma—The retinoid related compounds (4-hydroxphenylretinamide, AGN 193198) bind RAR and RXR weakly, yet have potent bioactivity. AGN 193198 (1 μM) potently induces growth arrest and apoptosis of bladder epithelial carcinoma lines (Reitmair et al., 2005, Retinoid-related molecule AGN193198 potently induces G2M arrest and apoptosis in bladder cancer cells. Int. J. Cancer (DOI10.1002/ijc.20961; in press). The mechanism of action for these RRMs is unclear.

Epithelial Cancer—AGN 193109 (10 nM, 100 nM) suppresses retinoid-mediated activities (proliferation, keratin & RARβ gene expression) in cultures of the human cervical cancer cell line ECE16-1 (Agarwal et al., 1996, AGN193109 is a highly effective antagonist of retinoid action in human ectocervical epithelial cells. J. Biol. Chem. 271:12209-12212). Against the potent RAR agonist TTNPB, AGN 193109 showed half-maximal suppression at a ratio of 1:1, and complete suppression of RAR activity at 10:1. AGN193109 did not have partial agonist activity in these studies. In regulating the gene expression of cultured normal human keratinocytes, AGN 193109 acts as an inverse agonist to compete against retinoid at a ratio of 10:1 (Thacher et al., 1999, Cell type and gene-specific activity of the retinoid inverse agonist AGN 193109: divergent effects from agonist at retinoic acid receptor γ in human keratinocytes. Cell Growth Diff 10:255-262). Data in this study also suggest that the agonist, inverse agonist, and antagonist may induce different functional states of the retinoid receptor.

Prostate Carcinoma—RAR antagonists caused the growth arrest and apoptosis of established prostate carcinoma cell lines, indicating a possible chemotherapeutic action for these compounds (Hammond et al., 2001, Antagonists of retinoic acid receptors (RARs) are potent growth inhibitors of prostate carcinoma cells. Br. J. Cancer 85:453-462). The most potent was AGN 194310, which was 12-22-times more potent than all-trans-retinoic acid in inhibiting its action. Its ED50 was 16-34 nM. AGN 194310 also induced growth arrest and apoptosis in 14 primary cell cultures established from human prostate cancer patients (Keedwell et al., 2004, An antagonist of retinoic acid receptors more effectively inhibits growth of human prostate cancer cells than normal prostate epithelium. Br. J. Cancer 91:580-588), with IC50s ranging from 200 to 800 nM. The transformed cells were more sensitive than were non-transformed cells, heightening their usefulness as chemotherapeutics.

Acute Promyelocytic Leukemia—The antagonist BMS614 shows antagonism for RARα transactivation when at 100-fold molar excess to RA (Gehin et al., 1999, Structural basis for engineering of retinoic acid receptor isotype-selective agonists and antagonists. Chem. Biol. 6:519-529), and at best modestly against RARβ, and no antagonism against RARγ. Of the BMS agonist/antagonists (681, 453, 614, 411), only 411 showed no activity in the acute promyelocytic leukemia assay, in which RA triggers their differentiation (Chen et al., 1996, Two distinct actions of retinoid-receptor ligands. Nature 382:819-822).

In another embodiment, this invention provides neutralizing antibodies to inhibit the biological action of target protein or gene, or to bind and sequester a specific retinoid or other molecule bound with RBP. Blocking peptides can also be used to interrupt retinoid action. See supra for one example. In another embodiment of the invention, the antagonizing agents are antisense oligonucleotides. The antisense oligonucleotides preferably inhibit target expression by inhibiting translation of the target protein. In a further embodiment, the antagonizing agent is small interfering RNAs (siRNA, also known as RNAi, RNA interference nucleic acids). siRNA are double-stranded RNA molecules, typically 21 n.t. in length, that are homologous to the target gene and interfere with the target gene's activity.

An antibody suitable for the present invention may be a polyclonal antibody. Preferably, the antibody is a monoclonal antibody. The antibody may also be isoform-specific. The monoclonal antibody or binding fragment thereof of the invention may be Fab fragments, F(ab)2 fragments, Fab' fragments, F(ab')2 fragments, Fd fragments, Fd' fragments or Fv fragments. Domain antibodies (dAbs) (for review, see Holt et al., 2003, Trends in Biotechnology 21:484-490) are also suitable for the methods of the present invention.

Various methods of producing antibodies with a known antigen are well-known to those ordinarily skilled in the art (see for example, Harlow and Lane, 1988, Antibodies: A Laboratory Manual. Cold Spring Harbor Laboratory Press, Cold Spring Harbor, N.Y.; see also WO 01/25437). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In accordance with the present invention, the antibodies or binding fragments thereof may be characterized as those which are capable of specific binding to a retinoid or other small molecule, to a target protein or an antigenic fragment thereof, preferably to an epitope that is recognized by an antibody when the antibody is administered in vivo. Antibodies can be elicited in an animal host by immunization with a target protein-derived immunogenic component, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

The antibodies may be from humans, or from animals other than humans, preferably mammals, such as rat, mouse, guinea pig, rabbit, goat, sheep, and pig, or avian species such as chicken. Preferred are mouse monoclonal antibodies and antigen-binding fragments or portions thereof. In addition, chimeric antibodies and hybrid antibodies are embraced by the present invention. Techniques for the production of chimeric antibodies are described in e.g. Morrison et al., 1984, Proc. Natl. Acad. Sci. USA, 81:6851-6855; Neuberger et al., 1984, Nature, 312:604-608; and Takeda et al., 1985, Nature, 314:452-454. For human therapeutic purposes, humanized, or more preferably, human antibodies are used.

Further, single chain antibodies are also suitable for the present invention (e.g., U.S. Pat. Nos. 5,476,786 and 5,132, 405 to Huston; Huston et al., 1988, Proc. Natl. Acad. Sci. USA, 85:5879-5883; U.S. Pat. No. 4,946,778 to Ladner et al.; Bird, 1988, Science, 242:423-426 and Ward et al., 1989, Nature, 334:544-546). Single chain antibodies are formed by linking the heavy and light immunoglobulin chain fragments of the Fv region via an amino acid bridge, resulting in a single chain polypeptide. Univalent antibodies are also embraced by the present invention.

Many routes of delivery are known to the skilled artisan for delivery of anti-target antibodies. For example, direct injection may be suitable for delivering the antibody to the site of interest. It is also possible to utilize liposomes with antibodies in their membranes to specifically deliver the liposome to the area where target gene expression or function is to be inhibited. These liposomes can be produced such that they contain, in addition to monoclonal antibody, other therapeutic agents, such as those described above, which would then be released at the target site (e.g., Wolff et al., 1984, Biochem. et Biophys. Acta, 802:259).

This invention also provides antisense nucleic acid molecules and compositions comprising such antisense molecules. The constitutive expression of antisense RNA in cells has been known to inhibit gene expression, possibly via blockage of translation or prevention of splicing. Interference with splicing allows the use of intron sequences which should be less conserved and therefore result in greater specificity, inhibiting expression of a gene product of one species but not its homologue in another species.

The term antisense component corresponds to an RNA sequence as well as a DNA sequence, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. This antisense molecule must have sufficient complementarity, about 18-30 nucleotides in length, to the target gene so that the antisense RNA can hybridize to the target gene (or mRNA) and inhibit target gene expression regardless of whether the action is at the level of splicing, transcription, or translation. The antisense components of the present invention may be hybridizable to any of several portions of the target cDNA, including the coding sequence, 3' or 5' untranslated regions, or other intronic sequences, or to target mRNA.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. In one embodiment, stable transfection and constitutive expression of vectors containing target cDNA fragments in the antisense orientation are achieved, or such expression may be under the control of tissue or development-specific promoters. Delivery can also be achieved by liposomes.

For in vivo therapy, the currently preferred method is direct delivery of antisense oligonucleotides, instead of stable transfection of an antisense cDNA fragment constructed into an expression vector. Antisense oligonucleotides having a size of 15-30 bases in length and with sequences hybridizable to any of several portions of the target cDNA, including the coding sequence, 3' or 5' untranslated regions, or other intronic sequences, or to target mRNA, are preferred. Sequences for the antisense oligonucleotides to target are preferably selected as being the ones that have the most potent antisense effects. Factors that govern a target site for the antisense oligonucleotide sequence include the length of the oligonucleotide, binding affinity, and accessibility of the target sequence. Sequences may be screened in vitro for potency of their antisense activity by measuring inhibition of target protein translation and target related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

The preferred target antisense oligonucleotides are those oligonucleotides which are stable, have a high resistance to nucleases, possess suitable pharmacokinetics to allow them to traffic to target tissue site at non-toxic doses, and have the ability to cross through plasma membranes.

Phosphorothioate antisense oligonucleotides may be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

The delivery route will be the one that provides the best antisense effect as measured according to the criteria described above. In vitro and in vivo assays using antisense oligonucleotides have shown that delivery mediated by cationic liposomes, by retroviral vectors and direct delivery are efficient. Another possible delivery mode is targeting using antibody to cell surface markers for the target cells. Antibody to target or to its receptor may serve this purpose.

Alternatively, nucleic acid sequences which inhibit or interfere with gene expression (e.g., siRNA, ribozymes, aptamers) can be used to inhibit or interfere with the activity of RNA or DNA encoding a target protein.

siRNA technology relates to a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the siRNA (sequence-specific) pathway, the initiating dsRNA is first broken into short interfering (si) RNAs, as described above. The siRNAs have sense and antisense strands of about 21 nucleotides that form approximately 19 nucleotide siRNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2',5' oligoadenylate synthetase (2',5'-AS), which synthesizes a molecule that activates RNase L, a nonspecific enzyme that targets all mRNAs. The nonspecific pathway may represent a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are preferred to effect gene repression by RNAi (see Hunter et al., 1975, J. Biol. Chem. 250:409-17; Manche et al., 1992, Mol. Cell. Biol. 12:5239-48; Minks et al., 1979, J. Biol. Chem. 254:10180-3; and Elbashir et al., 2001, Nature 411:494-8). siRNA has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass, 2001, Nature 411:428-9). In mammalian cells, siRNAs are effective at concentrations that are several orders of magnitude below the concentrations typically used in antisense experiments (Elbashir et al., 2001, Nature 411:494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., 2001, Nature 411:494-8).

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan.

Exemplary dsRNAs may be synthesized chemically or produced in vitro or in vivo using appropriate expression vectors. Exemplary synthetic RNAs include 21 nucleotide RNAs chemically synthesized using methods known in the art. Synthetic oligonucleotides are preferably deprotected and gel-purified using methods known in the art (see e.g. Elbashir et al., 2001, Genes Dev. 15:188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a target nucleic acid.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Although mRNAs are generally thought of as linear molecules containing the information for directing protein synthesis within the sequence of ribonucleotides, most mRNAs have been shown to contain a number of secondary and tertiary structures. Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al., 1989, Proc. Natl. Acad. Sci. USA 86:7706; and Turner et al., 1988, Annu. Rev. Biophys. Biophys. Chem. 17:167). The rules are useful in identification of RNA structural elements and, in particular, for identifying single stranded RNA regions which may represent preferred segments of the mRNA to target for siRNA, ribozyme or antisense technologies. Accordingly, preferred segments of the mRNA target can be identified for design of the siRNA mediating dsRNA oligonucleotides as well as for design of appropriate ribozyme and hammerheadribozyme compositions of the invention (see below).

The dsRNA oligonucleotides may be introduced into the cell by transfection with a heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141:863-74). The effectiveness of the siRNA may be assessed by any of a number of assays following introduction of the dsRNAs. These include Western blot analysis using antibodies which recognize the target gene product following sufficient time for turnover of the endogenous pool after new protein synthesis is repressed, reverse transcriptase polymerase chain reaction and Northern blot analysis to determine the level of existing target mRNA.

Further compositions, methods and applications of siRNA technology are provided in U.S. Pat. Nos. 6,278,039, 5,723,750 and 5,244,805, which are incorporated herein by reference.

Ribozymes are enzymatic RNA molecules capable of catalyzing specific cleavage of RNA. (For a review, see Rossi, 1994, Current Biology 4:469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to a target mRNA, and the well known catalytic sequence responsible for mRNA cleavage or a functionally equivalent sequence (see, e.g., U.S. Pat. No. 5,093,246, which is incorporated herein by reference in its entirety). Ribozyme molecules designed to catalytically cleave target mRNA transcripts can also be used to prevent translation of subject target mRNAs.

While ribozymes that cleave mRNA at site-specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach, 1988, Nature 334:585-591; and PCT Application. No. WO89/05852, the contents of which are incorporated herein by reference. Hammerhead ribozyme sequences can be embedded in a stable RNA such as a transfer RNA (tRNA) to increase cleavage efficiency in vivo (Perriman et al., 1995, Proc. Natl. Acad. Sci. USA, 92:6175-79; de Feyter, and Gaudron, Methods in Molecular Biology, Vol. 74, Chapter 43, "Expressing Ribozymes in Plants", Edited by Turner, P. C, Humana Press Inc., Totowa, N.J). In particular, RNA polymerase III-mediated expression of tRNA fusion ribozymes are well known in the art (see Kawasaki et al., 1998, Nature 393:284-9; Kuwabara et al., 1998, Nature Biotechnol. 16:961-5; and Kuwabara et al., 1998, Mol. Cell 2:617-27; Koseki et al., 1999, J. Virol 73:1868-77; Kuwabara et al., 1999, Proc. Natl. Acad. Sci. USA, 96:1886-91; Tanabe et al., 2000, Nature 406:473-4). There are typically a number of potential hammerhead ribozyme cleavage sites within a given target cDNA sequence. Preferably the ribozyme is engineered so that the cleavage recognition site is located near the 5' end of the target mRNA- to increase efficiency and minimize the intracellular accumulation of non-functional mRNA transcripts. Furthermore, the use of any cleavage recognition site located in the target sequence encoding different portions of the target mRNA would allow the selective targeting of one or the other target genes.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

The ribozymes of the present invention also include RNA endoribonucleases ("Cech-type ribozymes") such as the one which occurs naturally in *Tetrahymena thermophila* (known as the IVS, or L-19 IVS RNA) and which has been extensively described in Zaug, et al., 1984, Science, 224:574-578; Zaug, et al., 1986, Science 231:470-475; Zaug, et al., 1986, Nature 324:429-433; published International patent application No. WO88/04300; and Been, et al., 1986, Cell 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

In certain embodiments, a ribozyme may be designed by first identifying a sequence portion sufficient to cause effective knockdown by RNAi. The same sequence portion may then be incorporated into a ribozyme. In this aspect of the invention, the gene-targeting portions of the ribozyme or siRNA are substantially the same sequence of at least 5 and preferably 6, 7, 8, 9, 10, 11, 12, 13, 14, 15, 16, 17, 18, 19 or 20 or more contiguous nucleotides of a target nucleic acid.

In a long target RNA chain, significant numbers of target sites are not accessible to the ribozyme because they are hidden within secondary or tertiary structures (Birikh et al., 1997, Eur. J. Biochem. 245:1-16). To overcome the problem of target RNA accessibility, computer generated predictions of secondary structure are typically used to identify targets that are most likely to be single-stranded or have an "open" configuration (see Jaeger et al., 1989, Methods Enzymol. 183:281-306). Other approaches utilize a systematic approach to predicting secondary structure which involves assessing a huge number of candidate hybridizing oligonucleotides molecules (see Milner et al., 1997, Nat. Biotechnol. 15: 537-41; and Patzel and Sczakiel, 1998, Nat. Biotechnol. 16:64-8). Additionally, U.S. Pat. No. 6,251,588, the contents of which are herein incorporated by reference, describes methods for evaluating oligonucleotide probe sequences so as to predict the potential for hybridization to a target nucleic acid sequence. The method of the invention provides for the use of such methods to select preferred segments of a target mRNA sequence that are predicted to be single-stranded and, further, for the opportunistic utilization of the same or substantially identical target mRNA sequence, preferably comprising about 10-20 consecutive nucleotides of the target mRNA, in the design of both the siRNA oligonucleotides and ribozymes of the invention.

Alternatively, target gene expression can be reduced by targeting deoxyribonucleotide sequences complementary to the regulatory region of the gene (i.e., the promoter and/or enhancers) to form triple helical structures that prevent transcription of the gene in target cells in the body. (See generally, Helene, C., 1991, Anticancer Drug Des., 6:569-84; Helene, C., et al., 1992, Ann. N.Y. Acad. Sci., 660:27-36; and Maher, L. J., 1992, Bioassays 14:807-15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the target sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

A further aspect of the invention relates to the use of DNA enzymes to inhibit expression of target gene. DNA enzymes incorporate some of the mechanistic features of both antisense and ribozyme technologies. DNA enzymes are designed so that they recognize a particular target nucleic acid sequence, much like an antisense oligonucleotide. They are, however, catalytic and specifically cleave the target nucleic acid.

There are currently two basic types of DNA enzymes, both of which were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo are similar methods of delivery RNA ribozyme, as outlined in detail above. Additionally, one of skill in the art will recognize that, like antisense oligonucleotide, DNA enzymes can be optionally modified to improve stability and improve resistance to degradation.

The dosage ranges for the administration of the antagonists of the invention are those large enough to produce the desired effect. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication.

The antagonists of the invention can be administered parenterally by injection or by gradual perfusion over time. The antagonists can be administered intravenously, intraperitoneally, intramuscularly, subcutaneously, intracavity, or transdermally.

Another embodiment of the present invention relates to pharmaceutical compositions comprising one or more antagonists according to the invention, together with a physiologically- and/or pharmaceutically-acceptable carrier, excipient, or diluent. Physiologically acceptable carriers, excipients, or stabilizers are known to those skilled in the art (see Remington's Pharmaceutical Sciences, 17th edition, (Ed.) A. Osol, Mack Publishing Company, Easton, Pa., 1985). Acceptable carriers, excipients or stabilizers are nontoxic to recipients at the dosages and concentrations employed, and include buffers such as phosphate, citrate, and other organic acids; hydrophobic oils derived from natural or synthetic sources; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

In yet a further embodiment, the present invention provides small molecule antagonists and methods for using them to reduce or silence retinoid signaling pathways. The design of small molecule antagonists are known to one skilled in the art. One example of antagonists is the class of compounds that suppress the function of RARs or RXRs through their direct binding to these proteins (see e.g. Dawson and Zhang, 2002, Discovery and design of retinoic acid receptor and retinoid X receptor class- and subtype-selective synthetic analogs of all-trans-retinoic acid and 9-cis-retinoic acid, Current Med. Chem. 9:623-637, and Zhang et al., 1995, Evidence for the involvement of retinoic acid receptor RAR alpha-dependent signaling pathway in the induction of tissue transglutaminase and apoptosis by retinoids J. Biol. Chem. 270:6022-6029). Another example is the retinoid-neutral agonist compounds that reduce the activities of RAR, RXR, or related receptors (Johnson et al., 1999, Retinoid X receptor (RXR) agonist-induced activation of dominant-negative RXR-retinoic acid receptor alpha403 heterodimers is developmentally regulated during myeloid differentiation. Mol. Cell. Biol. 19:3372-3382). RAR and RXR signaling is regulated by histone acetylases and deacetylases. Their function can be interrupted by application of pharmaceutical agents that suppress HAc or activate HDAc for retinoid receptors.

Retinoid receptors require RA ligand to transduce signaling. Accordingly, in another embodiment, methods of the present invention manipulate levels of these ligands through effects on enzymes that synthesize or catabolize these ligands (for a list of examples of such ligands, see supra). Such compounds could also include citral, disulfuram, and others known to those skilled in the art. Another approach is to enhance the activity of enzymes that catabolize and remove RA, such as Cyp26 members. A third approach is to manipulate the levels of intracellular proteins that bind retinol or retinoic acid to control their concentrations in the nucleus. A fourth approach is to administer a blocking antibody against ligands such as retinoic acid, to reduce its activity within a tissue. For example, antibodies to retinoic acid is known in the art, see e.g. Twal, Roze and Zile, 1995, Anti-retinoic acid monoclonal antibody localizes all-trans-retinoic acid in target cells and blocks normal development in early quail embryo. Dev. Biol. 168:225-234.

Because a major source of retinoid is dietary intake, one method to lower RA levels is to reduce dietary retinoid intake through dietary manipulation. A second method is to block retinoid absorption in the gut. A third method is to administer an inhibitor of the enzyme that cleaves carotenoids to generate retinoid. A fourth method is to inhibit the esterases and other enzymes that convert retinoids into forms that can be transported from gut mucosa to the rest of the body.

Another major retinoid source is from body stores in liver, adipose and other tissues, the release from which is regulated by retinoid feedback. Antagonists of that feedback or of release of retinoid stores may be used to reduce retinoid levels in heart. Another method is to reduce the half-life of circulating retinoid by enhancing the renal or hepatic disposal of the retinoid.

EXAMPLES

Example 1

RBP Null Knock-Out Mice Have Healthier Hearts Than Wild-Type Mice a. General Observations Mice that harbor a null mutation in RBP were used to study myocardial development. These animals at the embryonic stages show a transient impairment of myocardial development, precocious differention of subepicardial cardiac myocytes, increased numbers of mesenchymal cells in outflow tract, and remarkably augmented fibronectin deposition in the cardiac jelly. At adult stages, echocardiography shows progressive cardiovascular changes including increased left ventricular mass and wall thickness, increased lumenal diameter, and impaired cardiac relaxation suggestive of cardiac hypertrophy. However, although classical clinical-hypertrophy is highlighted by increased up-regulation of embryonic cardiac genes, the gene expression pattern of the RBP-null mice showed a significant down-regulation of the embryonic hypertrophy marker genes. Moreover, the diameter of the cardiac myocytes was unchanged, whereas in classical myocardial clinical hypertrophy the diameter of the cardiac myocytes is increased. These results indicate that in RBP-null mice, clinical hypertrophy is inhibited, thereby suggesting that clinical hypertrophy may be inhibited by inhibiting transport of vitamin A. In other words, although heart enlargement was observed, RBP-null mice showed a failure or significant attenuation of the heart to up-regulate hypertrophy signals, and a normalized diameter of cardiac myocytes, features consistent with suppression of cardiac hypertrophy mechanisms.

b. Measurements and Comparison of Markers

At birth the heart weight of RBP-null mice is normal. However, by age 8 wks RBP-null mice had significantly enlarged hearts. Hence the heart enlargement due to RBP loss is postnatal.

Echocardiography and direct physical measurement suggest enlarged left ventricle and statistically significant reduction in percent fractional shortening (e.g. the heart doesn't relax fully). However, pressure-volume loop assessment of the RBP null hearts demonstrates that this is because the larger hearts achieve a larger stroke volume, meaning that they can circulate more blood without working as hard. There is no indication of congestive heart failure. The bottom line: contractile function is normal, and perhaps enhanced, in the RBP null hearts.

Detailed examination of RBP hearts finds no evidence for a pathological appearance. There is no necrosis or apoptosis, no sign of fibrosis or amyloidosis, and no inflammatory infiltrate. TGF-beta2 transcript levels are normal. We conclude that the enlargement does not reflect restrictive cardiomyopathy. The histological condition of RBP-null heart tissue is healthy.

The expression of cardiac hypertrophy markers was assessed to ascertain whether the heart enlargement reflects physiological or pathological hypertrophy. Two independent sets of mice were examined. Messenger RNA levels for hypertrophy markers were quantified by real-time PCR and normalized to β-actin; values are expressed as a percentage increase relative to age- and gender-matched wild-type controls. Overall there is a significant reduction in the expression of those genes that participate in pathological hypertrophy; α-skeletal actin is consistently and strongly suppressed; atrial naturetic factor and β-myosin heavy chain are reduced in one group or the other. In contradistinction, α-myosin heavy chain and Serca2a are elevated during physiological ("good") hypertrophy, such as exercise. α-MHC and, less consistently Serca2a, have elevated expression in the RBP-null mice. Overall these findings indicate that the heart enlargement in RBP-null mice is due to the induction of "good" hypertrophy responses, whereas the age-related progression of pathological hypertrophy progression is suppressed in the RBP-null mice. In summary, the RBP-null mice have a desirable cardiac gene expression profile.

The above data indicate that RBP-null mutation represents a "healthier" heart than that of wild-type littermates. The age-related progression of heart deterioration appeared to be arrested or delayed in the null mice. We tested this formally by subjecting mice to an overt cardiac stress, placing a constricting band around the aorta. This is a classic model of pressure overload and results in activation of pathological hypertrophy responses, heart enlargement, and ultimately heart failure.

TABLE 3

Comparison of Hypertrophy Marker Expression Between RBP-Null and Wild Type Mice

|  |  | Group 1 | Group 2 |
|---|---|---|---|
| Pathological Markers | Atrial naturetic factor | 68% ± 19% | 135% ± 45% |
|  | β-myosin heavy chain | 94% ± 70% | 58% ± 30% |
|  | α-skeletal actin | 34% ± 17% | 36% ± 22% |
| Physiological Markers | α-myosin heavy chain | 145% ± 11% | 150% ± 48% |
|  | Serca2a | 133% ± 9% | 76% ± 20% |

Group 1 consists of 5 WT and 3 null, age 10 months;
group 2 consists of 8 WT and 7 to 8 null, age 11-13 months.

c. Aortic Banding Experiments

RBP null and wild-type littermates at age 8 wks were subjected to aortic banding. Three weeks later, mice were echocardiographed to confirm that the banding was successful. Mice were then killed and cardiac hypertrophy was quantified. Overall these data show that, while wild-type mice show the expected cardiac enlargement caused by aortic banding, hearts of RBP-null mice fail to further enlarge. In summary, while banding of wild-type mice caused the predicted pathological hypertrophy response, banding of RBP-null mice failed to activate the pathological hypertrophy pathways.

TABLE 4

Summary of Aortic Banding Results

| | Left ventricular wet weight (mg)/tibia length (mm) | | |
|---|---|---|---|
|  | Unbanded mice | Banded mice | p value |
| Wild-type | 4.06 ± 0.30 | 4.77 ± 0.39 | 0.002 |
| RBP null | 4.68 ± 0.42 | 4.89 ± 0.30 | 0.355 |
| p-value | 0.003 | 0.611 |  |

* N of 5-6 female mice per group. P values are ANOVA and shown next to each pair-wise comparison, reading across or down.

While not willing to be bound by any theory, the present inventors believe that the responses of the RBP-null mutant mice are due to their lower serum vitamin A levels (15% to 20% of control values) and a subsequent reduction of retinoid-mediated signaling in heart.

Example 2

Expression Of Hypertrophy Markers In The Hearts Of RBP-Null And RBP-Wild-Type Mice As shown in Table 3 above, the hearts of mice deficient in RBP and retinoid signaling have a suppression of marker genes that are strongly correlated with pathogenic hypertrophy (atrial natriuretic factor, myosin heavy chain-beta, alpha-skeletal actin), and that these same hearts have an up-regulation in expression of marker genes that are strongly correlated with physiological hypertrophy (sarcoplasmic reticulum calcium ATPase-2a; myosin heavy chain-alpha). Therefore, the modest hypertrophy in the RBP-null mice reflects the activation of physiological ("good") hypertrophy responses. In other words, RBP-deficiency and the resultant retinoid-insufficiency caused by the loss of RBP, activate physiological hypertrophy responses and suppress the pathological ("bad") hypertrophy responses.

Furthermore, in RBP-null mice that had a severe pulmonary or circulatory problem, their expression of the pathological hypertrophy markers is lower than would be expected (Table 6). Thus, the loss of RBP and retinoid attenuates the progression of pathological hypertrophy, such that the heart can function better than it might otherwise.

TABLE 6

Comparison of mRNA Levels of Hypertrophy Markers in RBP-null Mouse Hearts that Experience Profound Cardiovascular Impairment With Wild-type Mouse Heart

| β-actin | 100 ± 0% | (control to normalize expression |
|---|---|---|
| ANF | 296 ± 130% | (pathological hypertrophy marker) |
| β-MHC | 617 ± 266% | (pathological hypertrophy marker) |
| α-SKA | 164 ± 2% | (pathological hypertrophy marker) |
| Serca-2A | 87 ± 14% | (physiological hypertrophy marker) |
| α-MHC | 114 ± 1% | (physiological hypertrophy marker) |

Table 7 shows additional evidence in RBP-null mice that their hypertrophy involves physiological and not pathological hypertrophy responses. Left ventricular expression of 7 hypertrophy markers was assessed in otherwise normal, 8 RBP-wild-type and 10-11 RBP-null mutant mice at 10-12 months of age. This was performed using real-time PCR, and data were normalized to β-actin expression prior to analysis by genotype. These data include (n=3) and significantly expand the previously disclosed data set presented as Group 1 in Table 3. Data in Table 7 demonstrate that mice that lack expression of RBP, and thus were in a state of subclinical vitamin A deficiency, exhibit a marked suppression of several genes known to be associated with the onset and progression of pathological hypertrophy (βMHC, α-SkA, MCIP). These mice also lacked the histological signs of such progression (no fibrosis, no infiltration, no amyloidosis). These mice were aged 10-12 months and should have exhibited such markers due to age-related reductions of cardiac function; however, they lack such an exhibition. Furthermore, these mice had a trend toward increased expression of a marker known to be associated with good (physiological) hypertrophy responses (αMHC). A loss of RBP and retinoid signaling may be responsible for an uncoupling of certain signaling pathways that govern hypertrophy responses.

TABLE 7

Additional evidence in RBP-null mice that hypertrophy involves physiological and not pathological hypertrophy responses

| | Expression Relative to WT Mice |
|---|---|
| Pathological Hypertrophy Markers (n = 8) | |
| Atrial Naturetic Factor (ANF) | 115% ± 44% (10) |
| β-myosin heavy chain (βMHC) | 69% ± 49% (10) p = 0.029 |
| α-skeletal actin (α-SkA) | 36% ± 20% (11) p = 0.007 |
| Muscle calcineurin interacting protein | 74% ± 26% (10) p = 0.102 |
| Calcineurin | 88% ± 26% (11) |
| Physiological Hypertrophy Markers | |
| α-myosin heavy chain (αMHC) | 175% ± 73% (11) p = 0.062 |
| Serca2a | 92% ± 25% (11) |

Example 3

Compared to Vitamin A-Sufficient Mice, Vitamin A-Deficient Mice Have a Significantly Diminished Hypertrophy Response to Pressure Overload A reduction of retinoid-dependent signaling improves cardiac function and attenuates hypertrophy responses in the presence of a cardiac stress. Specifically, vitamin A insufficiency through dietary manipulation of vitamin A intake, protects the heart from pathological hypertrophy.

Experimental Design. Genetically normal, C57B1/6J mice, both sexes, were reared to dams fed a vitamin A-deficient diet from gestational day 17 through birth and lactation. At postnatal day 18, mice were weaned and assigned to a vitamin A-free diet, or a diet containing 25,000 IU vitamin A (as retinyl palmitate). This latter is an adequate intake for mouse. At 8 weeks of age, half the mice were subjected to surgery in which a constrictive band was placed to encircle the aorta. At 11 wks of age, all mice were killed. Serum and liver were collected for retinoid content. Heart weights, left ventricular weights, and tibia lengths were measured to document the severity of hypertrophy. Hearts were frozen for later molecular analysis.

Results. Male and female mice were analyzed separately due to a gender effect on heart size that was distinct from banding and dietary treatment effects. Results are presented in Table 8 as Left Ventricular Wt (mg)/tibia length (mm).

TABLE 8

Comparison of Left Ventricular Weight/tibia length (mg/mm) in Male and Female Mice on VA-Sufficient and VA-deficient diet

| | Unbanded | Banded | |
|---|---|---|---|
| Female Mice Results: | | | |
| VA-Sufficient | 4.76 ± 0.36 (9) | 7.18 ± 1.06 (8) | p < 0.0001 |
| VA-Deficient | 5.29 ± 0.45 (10) p = 0.012 | 5.88 ± 1.13 (10) p = 0.025 | p = 0.137 |
| Male Mice Results: | | | |
| VA-Sufficient | 5.58 ± 0.39 (10) | 7.20 ± 0.79 (10) | p < 0.0001 |
| VA-Deficient | 5.73 ± 0.52 (7) p = 0.569 | 6.46 ± 0.41 (6) p = 0.056 | p = 0.018 |

The above results showed that aortic banding by surgical constriction caused significant cardiac hypertrophy ($p<0.0001$) in Vitamin A sufficient animals, for both males and females. This confirms that the technique works to induce cardiac overload and hypertrophy.

The results further demonstrate that dietary vitamin A deficiency caused cardiac enlargement in female mice, as compared with VA-sufficient females of identical age and genetic background (p=0.012). This observation replicates the observation in RBP-null mutant mice, and suggests that the RBP effect is attributed to vitamin A insufficiency. Cardiac enlargement was not observed in male VAD mice (p=0.569). The sex dichotomy likely reflects gender differences in vitamin A clearance, as these males and females were littermates.

Importantly, female mice reared on a vitamin A-deficient diet are resistant to pressure overload-induced cardiac hypertrophy, as compared with vitamin A-adequate mice (p=0.137). An attenuated hypertrophy response is seen in vitamin A deficient males (p=0.018 for VAD banded vs. unbanded; p=0.056 for VAD vs. VAS banded mice).

Example 4

Loss of RBP or Retinoid Signaling Suppresses Hypertrophy Responses as Measured by Cardiomyocyte Diameter Hearts of 5-month old WT or RBP-null mice were fixed in end-stage diastole, at a uniform state of contraction. Hearts were sectioned. Cardiomyocytes were visualized with antibody against α-skeletal actin, their diameter was defined by staining with an antibody against laminin, and nuclei were visualized by DAPI staining. Cross-sectional diameter of α-skeletal actin-positive cells was ascertained at the level of the nucleus, using the method and criteria of Oh et al., 2001, Telomerase reverse transcriptase promotes cardiac muscle cell proliferation, hypertrophy, and survival. Proc. Natl. Acad. Sci. USA 98:10308-10313. The cross-sectional area per myocyte for RBP-Wild-type was 2336±174, compared to 2299±255 RBP-null. The difference is not significant with a p=0.817.

The progression of pathological hypertrophy is associated with increased diameter of the cardiomyocyte; this reflects their increased content of contractile protein. The lack of enhanced cardiomyocyte diameter in RBP-null mice, despite the increased size of their hearts, offers further evidence that the mechanism does not involve the induction of pathological hypertrophy signals.

Example 5

Loss of RBP or Retinoid Signaling does not Impair Cardiac Function as Determined by Load-Independent Assessment of RBP-Null Heart Function Five-month old wild-type or RBP-null mice were subjected to intravenous insertion of a pressure impedance catheter into their left ventricle. Cardiac function was documented across the contraction cycle, in anaesthetized mice and in the same animals with inotropic challenge.

Responses were measured and are shown in Table 9, expressed as the percentage of KO response relative to WT response (p in parenthesis).

The above results show that measures of cardiac stress (ESPVR, EDPVR, % FS) were largely indistinguishable between RBP WT and Null hearts, both at rest and under contractile challenge. This indicates that the RBP-null hearts are not failing, and do not have increased stiffness or contractile impairment. In fact, there is a trend toward improved function of the RBP-null vs. WT hearts, as reflected in their significant increase in Ved and trend to increased SV. Cardiac output was greater in the RBP null animals but this did not achieve significance. Overall, the loss of RBP is not deleterious to heart function, in that these hearts function normally to supranormally, as compared with their WT counterparts.

TABLE 9

Load-Independent Assessment Of RBP-Null Heart Function (Relative to WT Response)

|  | At Rest | Inotropic-Challenge |
| --- | --- | --- |
| % Fractional Shortening | 96% (0.36) | 94% (0.45) |
| Pressure-Volume Relation At End Systole | 105% (0.85) | 56% (0.65) |
| Pressure-Volume Relation At End Diastole | 81% (0.81) | 46% (0.03) |
| LV volume at End Diastole | 119% (0.05) | 125% (0.04) |
| Stroke Volume | 119% (0.06) | 118% (0.14) |
| Cardiac Output | 117% (0.19) | 125% (0.34) |

Example 6

Cardiomyocyte Proliferation is Enhanced in Hearts of Neonatal RBP-Null Mice as Compared with Wild-Type Littermates Hearts of WT and RBP-null littermates were collected and fixed at postnatal days 1 and 13. Cardiac sections were prepared and proliferating cardiomyocytes were visualized using antibody directed against acetylated phosphohistone H3. Cardiomyocyte identity was confirmed by counterstaining with α-sarcomeric actin. Approximately 1500 nuclei were sampled per heart, and N=4 mice per genotype and age.

TABLE 10

Comparison of Cardiomyocyte proliferation in hearts of neonatal RBP-null mice with wild-type littermates

| | % Phosphohistone-labeled myocytes Neonatal mice | |
| --- | --- | --- |
| PN1 | RBP-WT | 0.82% ± 0.21% (4) |
| | RBP-null | 2.82% ± 0.60% (4) |
| | | $P < 0.0001$ |
| PN13 | RBP-WT | 0.38% ± 0.18% (4) |
| | RBP-null | 1.40% ± 0.70% (4) |
| | | $P < 0.01$ |
| | 10 month old mice Total # Labeled Myocytes per Transverse Heart Section | |
| | RBP-WT | 1.7 ± 0.62 (3) |
| | RBP-KO | 2.5 ± 0.45 (3) |

These results show that RBP-null mutant hearts have enhanced numbers of proliferating cardiomyocytes at early postnatal days, but not in older adults.

Example 7

Use of Fenretinide for Treating Cardiac Hypertrophy

Fenretinide (N-[4-hydroxyphenyl]retinamide, 4HPR) is a retinoid analog, and is known to lower the concentrations of both vitamin A and retinol binding protein (RBP) in the bloodstream (Formelli et al. 1989, Plasma retinol level reduction by the synthetic retinoid fenretinide: a one year follow-up study of breast cancer patients. Cancer Res 48:6149-6152; Dimitrov et al. 1990, Alteration of retinol binding protein concentrations by the synthetic retinoid fenretinide in healthy human subjects. Am J Clin Nutr 51:1082-1087; Peng et al. 1989, Pharmacokinetics of N-4-hydroxyphenyl-retinamide and the effect of its oral administration on plasma retinol concentrations in cancer patients. Int. J. Cancer 43:22-26). This creates symptoms of vitamin A insufficiency, including impaired dark vision adaptation and epithelial keratosis (Kaiser-Kupfer et al. 1986, Abnormal retinal function associated with fenretinide, a synthetic retinoid. Arch Ophthalmol 104: 69-70). Because of this side effect, clinical practice is that patients abstain from fenretinide for several days each month to replete their serum vitamin A values.

Fenretinide has undergone extensive phase 2 and phase 3 clinical trials as a chemotherapeutic in diverse cancers of epithelial origin (reviewed in Cobleigh 1993, Breast cancer and fenretinide, an analogue of vitamin A. Leukemia 8:S59-S63; also see Moon et al. 1982, Influence of 15 retinoic acid amides on urinary bladder carcinogenesis in the mouse. Carcinogenesis 3:1469-1472; Moon et al. 1983, Inhibition of carcinogenesis by retinoids. Cancer Res. 43:2469S-2475S) and its mechanism of action is not entirely understood. However, it is well established that it binds to RBP, displacing RBP from transthyretin (TTR) and dramatically increasing renal losses of RBP and vitamin A (Holven et al. 1997, Secretion of N-(4-hydroxyphenyl) retinamide-retinol binding protein from liver paranchymal cells: evidence for reduced affinity of the complex for transthyretin. Int J Cancer 71:654-659; Malpeli et al. 1996, Retinoid binding to retinol-binding protein and the interference with the interaction with transthyretin. Biochim Biophys Acta 1294:48-54; Sani et al. 1995, N-(4-hydroxyphenyl) retinamide: interactions with retinoid-binding proteins/receptors. Carcinogen 16:2531-2534). Fenretinide poorly trans-activates the nuclear retinoid receptors (Sani et al. 1995).

In an embodiment, fenretinide is administered to a patient in need thereof for treating and/or preventing pathological cardiac hypertrophy, and cardiac failure. Administration of fenretinide results in improved contractile function, enhanced cardiomyocyte proliferation, and suppression of pathological hypertrophy responses to challenges such as pressure overload. Fenretinide is supplied as an oil-filled gelatin capsule and administered orally (Conley et al. 2000, Pilot trial of the safety, tolerability, and retinoid levels of N-(4-hydroxyphenyl) retinamide in combination with tamoxifen in patients at high risk for developing invasive breast cancer. J. Clin. Oncol. 18:275-283). Alternatively, it is incorporated into a liposome (Takahashi et al. 2003, Effects on M5076-hepatic metastasis of retinoic acid and N-(4-hydroxyphenyul) retinamide, fenretinide entrapped in SG-liposomes. Biol. Pharm. Bull. 26:1060-1063), or into an immunoliposome that is targeted to the desired tissue such as heart (Raffaghello et al., 2003, Immunoliposomal fenretinide: a novel antitumoral drug for human neuroblastoma. 197:151-152).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

REFERENCES

Altucci L, Wilhelm E, Gronemeyer H. Leukemia: beneficial actions of retinoids and rexinoids. Int J Biochem Cell Biol 36;178-182.
Apfel C, Bauer F, Crettaz M, Forni L, Kamber M, Kaufmann F, LeMotte P, Pirson W, Klaus M. 1992. A retinoic acid receptor a antagonist selective counteracts retinoic acid effects. Proc Natl Acad Sci USA 89:7129-7133.
Blomhoff R. 1994. Transport and metabolism of vitamin A. Nutr Rev. 52:S13-S23.
Colbert M C. 2002. Retinoids and cardiovascular developmental defects. Cardiovasc. Toxicol. 2:25-39.
Formelli F, Clerici M, Campa T, Di Mauro M G, Magni A, Mascotti G, Moglia D, De Palo G, Costa A, Veronesi U. 1993. Five-year administration of fenretinide: pharmacokinetics and effects on plasma retinol concentrations. J Clin Oncol 112036-2042.
Frey N, Olson E N. 2003. Cardiac hypertrophy: the good, the bad, and the ugly. Annu. Rev. Physiol. 65:45-79.
Gigure V. 1994. Retinoic acid receptors and cellular retinoid binding proteins: complex interplay in retinoid signaling. Endocrin. Rev. 15:61-79.
Klein E S, Wang J W, Khalifa B, Gavigan S A, Chandraratna R A S. 2000. Recruitment of nuclear receptor corepressor and coactivator to the retinoic acid receptor by retinoid ligands. J Biol Chem 275:19401-19408.
Kochhar D M, Jiang H, Penner J D, Johnson A T, Chandraratna R A S. 1998. The use of a retinoid receptor antagonist in a new model to study vitamin A-dependent developmental events. Int. J. Dev. Biol. 42601-608.
Nagpal S, Chandraratna R A S. 2000. Recent developments in receptor-sensitive retinoids. CurrPharm Design 6:919-931.
Napoli J L. 1996. Biochemical pathways of retinoid transport, metabolism, and signal transduction. Clin. Immunol. Immunopath. 80:S52-S62.
Moon R C, Constantinou A I. 1997. Dietary retinoids and carotenoids in rodent models of mammary tumorigenesis. Breast Cancer Res Treat 46:181-189.
Ross A C. 1991. Vitamin A: current understanding of the mechanisms of action. Nutr. Today 26:6-12.
Torrisi R, Pensa F, Orengo M A, Catsafados E, Ponzani P, Boccardo F, Costa A, Decensi A. 1993. The synthetic retinoid fenretinide lowers plasma insulin-like growth factor I levels in breast cancer patients. Cancer Res 53:4769-4771.
Zhou M D, Sucov H M, Evans R M, Chien K R. 1995. Retinoid-dependent pathways suppress myocardial cell hypertrophy. Proc. Natl. Acad. Sci. USA 92:7391-7395.

What is claimed is:

1. A method for treating cardiac hypertrophy in a mammal or higher vertebrate in need thereof, comprising administering to the mammal or higher vertebrate an effective amount of a pharmaceutical composition comprising N-[4-hydroxyphenyl]retinamide.

2. The method according to claim 1, wherein the method is for the treatment of pathological hypertrophy, chronic heart failure, restrictive cardiomyopathies, valvuloseptal disorders, ischemic heart disease, emphysema, atherosclerosis, amyloidosis, viral myocarditis, cardiac dilatation, and genetic syndromes of dysfunctional heart action.

3. The method according to claim 1, wherein the mammal is a human.

4. The method according to claim 1, wherein the higher vertebrate is a turkey.

* * * * *